(12) United States Patent
Dubé et al.

(10) Patent No.: US 8,563,241 B2
(45) Date of Patent: Oct. 22, 2013

(54) GENETIC PREDICTORS OF INTERNATIONAL NORMALIZED RATIO (INR) FLUCTUATION WITH WARFARIN THERAPY

(75) Inventors: Marie-Pierre Dubé, Montreal (CA); Hannah Beattie, Montreal (CA)

(73) Assignee: Institut de Cardiologie de Montreal, Montreal (CA)

( * ) Notice: Subject to any disclaimer, the term of this patent is extended or adjusted under 35 U.S.C. 154(b) by 558 days.

(21) Appl. No.: 12/801,248

(22) Filed: May 28, 2010

(65) Prior Publication Data

US 2010/0304393 A1     Dec. 2, 2010

Related U.S. Application Data

(60) Provisional application No. 61/213,311, filed on May 28, 2009.

(51) Int. Cl.
| | |
|---|---|
| *C12Q 1/68* | (2006.01) |
| *C12P 19/34* | (2006.01) |
| *C07H 21/02* | (2006.01) |
| *C07H 21/04* | (2006.01) |

(52) U.S. Cl.
USPC .......... 435/6.1; 435/91.1; 536/23.1; 536/24.3

(58) Field of Classification Search
None
See application file for complete search history.

(56) References Cited

U.S. PATENT DOCUMENTS 6,316,196 B1 * 11/2001 Morten .................. 435/6.14

OTHER PUBLICATIONS

Takahashi et al; The Pharmacogenomics Journal, vol. 3, pp. 202-214, 2003.*
Caldwell et al; Blood, vol. 111, pp. 4106-4112 Apr. 15, 2008.*
ss74829409 for rs6772976 (NCBI, NLM; 2007).*

* cited by examiner

*Primary Examiner* — Jehanne Sitton

(57) ABSTRACT

There are disclosed methods and kits for identifying a subject having genetic predictors of predisposition to abnormal international normalized ratio (INR) fluctuation during warfarin therapy. In an embodiment, a method includes testing the subject to check for a presence of a predetermined genetic variation. The predetermined genetic variation is correlated with abnormal INR fluctuation during warfarin therapy. The subject is identified as having a predisposition to abnormal INR fluctuation during warfarin therapy when the testing indicates the presence of the predetermined genetic variation. In one embodiment, a kit includes a test to check the subject for a presence of a predetermined genetic variation. The predetermined genetic variation is correlated with abnormal INR fluctuation during warfarin therapy. The kit includes an indicator to identify the presence of the predetermined genetic variation so as to identify the subject as having a predisposition to abnormal INR fluctuation during warfarin therapy.

11 Claims, 2 Drawing Sheets

FIGURE 2

| CHR | Gene | Position | SNP | Minor allele | MAF | N | % time outside target range | | % time above target range | | % time under target range | |
|---|---|---|---|---|---|---|---|---|---|---|---|---|
| | | | | | | | Genotype | Additive | Genotype | Additive | Genotype | Additive |
| 1 | NR1I3 | 159,469,228 | rs2307424 | T | 0.366 | 324 | 0.6760 | 0.6903 | 0.9318 | 0.7131 | 0.6623 | 0.8395 |
| 1 | NR1I3 | 159,470,840 | rs3003596 | G | 0.378 | 324 | 0.7268 | 0.5246 | 0.1142 | 0.0375 | 0.1756 | 0.0638 |
| 1 | EPHX1 | 224,061,833 | rs4653436 | A | 0.328 | 323 | 0.8314 | 0.5435 | 0.7506 | 0.6295 | 0.7008 | 0.6544 |
| 1 | EPHX1 | 224,062,734 | rs4559463 | A | 0.38 | 254 | 0.4550 | 0.2965 | 0.5651 | 0.3442 | 0.8731 | 0.9727 |
| 2 | GGCX | 85,640,851 | rs12714145 | T | 0.39 | 319 | 0.4758 | 0.8937 | 0.1855 | 0.7849 | 0.7405 | 0.7018 |
| 2 | PROC | 127,891,312 | rs2069901 | C | 0.41 | 318 | 0.3465 | 0.1451 | 0.4559 | 0.3070 | 0.7195 | 0.5758 |
| 2 | PROC | 127,896,022 | rs2069919 | A | 0.331 | 270 | 0.1468 | 0.2206 | 0.5758 | 0.9726 | 0.3655 | 0.4511 |
| 2 | PROC | 127,896,690 | rs973760 | A | 0.323 | 324 | 0.4308 | 0.3108 | 0.7833 | 0.7756 | 0.1421 | 0.2652 |
| 3 | NR1I2 | 120,987,070 | rs10934498 | G | 0.42 | 324 | 0.6862 | 0.6435 | 0.5054 | 0.4227 | 0.0669 | 0.1522 |
| 3 | NR1I2 | 121,002,153 | rs6772976 | A | 0.318 | 324 | 0.0954 | 0.1489 | 0.2188 | 0.0925 | 0.0011 | 0.0005 |
| 3 | NR1I2 | 121,002,814 | rs2461823 | A | 0.407 | 313 | 0.0370 | 0.1033 | 0.4150 | 0.2389 | 0.0043 | 0.0028 |
| 3 | NR1I2 | 121,008,186 | rs7643645 | G | 0.381 | 324 | 0.6806 | 0.3894 | 0.2125 | 0.0793 | 0.0119 | 0.0031 |
| 7 | ABCB1 | 86,976,580 | rs1045642 | C | 0.48 | 324 | 0.4833 | 0.2282 | 0.9714 | 0.8633 | 0.3305 | 0.1445 |
| 7 | ABCB1 | 87,017,536 | rs1128503 | T | 0.475 | 322 | 0.3041 | 0.1478 | 0.9362 | 0.8669 | 0.1198 | 0.0497 |
| 7 | ABCB1 | 87,017,744 | rs2229109 | A | 0.049 | 324 | 0.9235 | 0.9235 | 0.1848 | 0.1848 | 0.0562 | 0.0562 |
| 7 | CYP3A5 | 99,100,770 | rs10264272 (*6) | T | 0.003 | 324 | 0.9122 | 0.9122 | 0.5202 | 0.5202 | 0.4905 | 0.4905 |
| 7 | CYP3A5 | 99,108,474 | rs776746 (*3) | A | 0.061 | 320 | 0.0601 | 0.7047 | 0.1431 | 0.1787 | 0.0905 | 0.0862 |
| 10 | CYP2C9 | 96,692,036 | rs1799853 (*2) | T | 0.116 | 322 | 0.2738 | 0.9109 | 0.9096 | 0.9409 | 0.2285 | 0.9152 |
| 10 | CYP2C9 | 96,731,042 | rs1057910 (*3) | C | 0.068 | 322 | 0.9440 | 0.9473 | 0.8500 | 0.7436 | 0.6627 | 0.5366 |
| 16 | VKORC1 | 31,009,821 | rs7294 | A | 0.393 | 322 | 0.7968 | 0.6895 | 0.4749 | 0.3297 | 0.5534 | 0.2814 |
| 16 | VKORC1 | 31,010,089 | rs7200749 | T | 0.009 | 322 | 0.2488 | 0.8294 | 0.2479 | 0.1880 | 0.3745 | 0.2179 |
| 16 | VKORC1 | 31,011,296 | rs2359612 | T | 0.41 | 322 | 0.9898 | 0.8875 | 0.7325 | 0.4458 | 0.7349 | 0.4470 |
| 16 | VKORC1 | 31,012,009 | rs8050894 | C | 0.408 | 284 | 0.8873 | 0.6668 | 0.8831 | 0.6327 | 0.6772 | 0.3853 |
| 16 | VKORC1 | 31,012,378 | rs9934438 | T | 0.41 | 322 | 0.9898 | 0.8875 | 0.7325 | 0.4458 | 0.7349 | 0.4470 |
| 16 | VKORC1 | 31,012,853 | rs17708472 | T | 0.182 | 321 | 0.7069 | 0.8581 | 0.1684 | 0.8970 | 0.7963 | 0.9533 |
| 16 | VKORC1 | 31,013,054 | rs2884737 | G | 0.298 | 322 | 0.4478 | 0.6911 | 0.3384 | 0.2827 | 0.8492 | 0.7309 |
| 16 | VKORC1 | 31,015,189 | rs9923231 | A | 0.41 | 322 | 0.9898 | 0.8875 | 0.7325 | 0.4458 | 0.7349 | 0.4470 |
| 19 | CYP4F2 | 15,839,056 | rs12609820 | C | 0.361 | 295 | 0.6994 | 0.5706 | 0.5157 | 0.5952 | 0.5436 | 0.3821 |
| 19 | CYP4F2 | 15,851,430 | rs2108622 | T | 0.234 | 269 | 0.0416 | 0.8577 | 0.0005 | 0.3793 | 0.2442 | 0.0977 |
| 19 | CYP2A6 | 46,046,373 | rs60563539 (*3) | A | 0.002 | 290 | 0.9331 | 0.9331 | 0.8042 | 0.8042 | 0.7836 | 0.7836 |

General linear model (GLM) results showing p-values for genotypic and additive models with covariates age, gender and follow-up time; significance threshold is p<0.00088; CHR chromosome; SNP single nucleotide polymorphism; MAF minor allele frequency.

GENETIC PREDICTORS OF INTERNATIONAL NORMALIZED RATIO (INR) FLUCTUATION WITH WARFARIN THERAPY

REFERENCE TO PENDING PRIOR PATENT APPLICATION

This application claims the benefit under 35 U.S.C. 119 (e) of U.S. Provisional Patent Application Ser. No. 61/213,311, filed May 28, 2009, which patent application is hereby incorporated herein by reference.

FIELD OF THE INVENTION

The present invention relates to the general field of anticoagulant therapy and is particularly concerned with genetic predictors of international normalized ratio (INR) fluctuation with warfarin therapy.

BACKGROUND

Warfarin is the most widely prescribed oral anticoagulant for the treatment and prevention of thromboembolic diseases. The high inter-individual variability in warfarin dosing is an ongoing problem that is worsening as the population ages and eligible patients increase in numbers. Effectiveness and safety of warfarin therapy are routinely monitored by the international normalized ratio (INR), the ratio of time required for coagulation relative to a reference. More particularly, the international normalized ratio (INR) is a system for reporting the results of blood coagulation tests. For example, a person taking the anticoagulant warfarin might optimally maintain a prothrombin time of 2 to 3 INR. No matter what laboratory checks the prothrombin time, the result should be the same even if different thromboplastins and instruments are used. The international normalized ratio (INR) standardization permits patients on warfarin to obtain comparable test results at different locations.

Despite the large number of anticoagulation clinics and efficient INR monitoring programs, up to 15% of warfarin users suffer from bleeding and 11% from thromboembolic events that can lead to hospitalizations and deaths. INR fluctuations above the targeted therapeutic INR range in particular are associated with an accrued risk of bleeding. For every unit increase in INR, one study reported an increase in odds of major bleeding by 0.6 in younger patients and by 0.4 in older patients. In a hospital-based study, INR values $\geq 4$ were shown to be associated with a marked increase in bleeding risk (OR 13, 95% CI 1.2-150). Still, patients fluctuate above their target therapeutic INR range in as high as 30% of the time in the first 3 months of treatment, and 14% subsequently.

The relative contribution of different polymorphisms to warfarin dosing has already been studied in various patient populations and ethnic comparisons have been made. Most previous studies have focused on the use of genetic polymorphisms to predict stable therapeutic dose, the impact of the algorithm on the percentage of patients who are outside of the therapeutic range or the time to stable INR and warfarin dose. A question of immediate clinical relevance, however, is whether a patient's genetic information can be used to reduce the occurrence of serious clinical events due to warfarin treatment.

Against this background, there exists a need for a new and improved methods for reducing the occurrence of serious clinical events due to warfarin treatment.

SUMMARY OF THE INVENTION

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

In an embodiment, there is provided a method of identifying a subject having genetic predictors of predisposition to abnormal international normalized ratio (INR) fluctuation during warfarin therapy, the method comprising testing the subject to check for a presence of a predetermined genetic variation, wherein the predetermined genetic variation is correlated with abnormal INR fluctuation during warfarin therapy; and identifying the subject as having a predisposition to abnormal INR fluctuation during warfarin therapy when the testing indicates the presence of the predetermined genetic variation.

In some embodiments of the invention, the predetermined genetic variation is located in the CYP4F2 gene. For example, the predetermined genetic variation is a predetermined single nucleotide polymorphism (SNP) in the CYP4F2 gene, such as, non-limitingly, the predetermined SNP rs2108622.

In some embodiments of the invention, the predetermined SNP is correlated with the abnormal INR fluctuation being generally above a patient-specific target therapeutic INR range, and presence of the predetermined SNP identifies the subject as having a predisposition to the abnormal INR fluctuation being generally above the patient-specific target therapeutic INR range.

In some embodiments of the invention, the predetermined genetic variation is located in the NR1I2 gene. For example, the predetermined genetic variation is a predetermined single nucleotide polymorphism (SNP) in the NR1I2 gene, such as, non-limitingly, the predetermined SNP rs6772976.

In some embodiments of the invention, the predetermined SNP is correlated with the abnormal INR fluctuation being generally below a patient-specific target therapeutic INR range, and presence of the predetermined SNP identifies the subject as having a predisposition to the abnormal INR fluctuation being generally below the patient-specific target therapeutic INR range.

In a variant, the subject is human.

In some embodiments of the invention, the predetermined genetic variation is a predetermined single nucleotide polymorphism (SNP).

In some embodiments of the invention, the predetermined SNP is correlated with the abnormal INR fluctuation being generally below a patient-specific target therapeutic INR range, and presence of the predetermined SNP identifies the subject as having a predisposition to the abnormal INR fluctuation being generally below the patient-specific target therapeutic INR range. In other embodiments of the invention, the predetermined SNP is correlated with the abnormal INR fluctuation being generally above a patient-specific target therapeutic INR range, and presence of the predetermined SNP identifies the subject as having a predisposition to the abnormal INR fluctuation being generally above the patient-specific target therapeutic INR range.

In some embodiments of the invention, the predetermined SNP is correlated with the abnormal INR fluctuation being generally outside a patient-specific target therapeutic INR range, presence of the predetermined SNP identifies the subject as having a predisposition to the abnormal INR fluctuation being generally outside the patient-specific target therapeutic INR range, and wherein the patient-specific target therapeutic INR range is set to 2-3.

In other embodiments of the invention, the predetermined SNP is correlated with the abnormal INR fluctuation being generally outside a patient-specific target therapeutic INR range, presence of the predetermined SNP identifies the subject as having a predisposition to the abnormal INR fluctuation being generally outside the patient-specific target therapeutic INR range, and wherein the patient-specific target therapeutic INR range is set to 2.5-3.5.

In some embodiments of the invention, the predisposition to the abnormal INR fluctuation is during a post-stabilization period of the warfarin therapy.

In some embodiments of the invention, the step of identifying the subject as having the predisposition to abnormal INR fluctuation during warfarin therapy includes performing a hybridization reaction followed by fluorescence in situ hybridization.

In other embodiments of the invention, the step of identifying the subject as having the predisposition to abnormal INR fluctuation during warfarin therapy includes performing at least one of a DNA sequencing procedure, a PFGE analysis procedure, a Southern blot analysis procedure, a single stranded conformation analysis procedure, and a RNase protection assay procedure.

In another embodiment, there is provided a kit for identifying a subject having genetic predictors of predisposition to abnormal international normalized ratio (INR) fluctuation during warfarin therapy, the kit comprising a test to check the subject for a presence of a predetermined genetic variation, wherein the predetermined genetic variation is correlated with abnormal INR fluctuation during warfarin therapy; and an indicator to identify the presence of the predetermined genetic variation so as to identify the subject as having a predisposition to abnormal INR fluctuation during warfarin therapy.

In some embodiments of the invention, the test is configured to check the subject for the predetermined genetic variation in the CYP4F2 gene. For example, the test is configured to check the subject for the predetermined genetic variation in a predetermined single nucleotide polymorphism (SNP) in the CYP4F2 gene. In a specific embodiment, the predetermined SNP is rs2108622.

In some embodiments of the invention, the test is configured to check the subject for the predetermined genetic variation in the NR1I2 gene. For example, the test is configured to check the subject for the predetermined genetic variation in a predetermined single nucleotide polymorphism (SNP) in the NR1I2 gene. In a specific embodiment, In some embodiments of the invention, the patient-specific target therapeutic INR range is set to 2-3.

In some embodiments of the invention, the predetermined SNP is correlated with the abnormal INR fluctuation being generally outside a patient-specific target therapeutic INR range, presence of the predetermined SNP identifies the subject as having a predisposition to the abnormal INR fluctuation being generally outside the patient-specific target therapeutic INR range, and wherein the patient-specific target therapeutic INR range is set to 2-3.

In some embodiments of the invention, the predetermined SNP is correlated with the abnormal INR fluctuation being generally outside a patient-specific target therapeutic INR range, presence of the predetermined SNP identifies the subject as having a predisposition to the abnormal INR fluctuation being generally outside the patient-specific target therapeutic INR range, and wherein the patient-specific target therapeutic INR range is set to 2.5-3.5.

In some embodiments of the invention, the test to check the subject for the presence of the predetermined genetic variation is conducted during a post-stabilization period of the warfarin therapy.

In some embodiments of the invention, the test to check the subject for the presence of the predetermined genetic variation includes performing a hybridization reaction followed by fluorescence in situ hybridization. In other embodiments of the invention, the test to check the subject for the presence of the predetermined genetic variation performing at least one of a DNA sequencing procedure, a PFGE analysis procedure, a Southern blot analysis procedure, a single stranded conformation analysis procedure, and a RNase protection assay procedure.

Other embodiments are also disclosed.

In order to identify markers of increased likelihood of serious clinical events in patients subject to warfarin therapy, patients INR fluctuations above and below their therapeutic range was used as a surrogate endpoint of serious clinical event risk.

The Montreal Heart Institute (MHI) has a large anticoagulation clinic, which follows in excess of 4200 patients on long-term warfarin therapy. Patients attending this clinic were recruited to participate in a study aimed at uncovering the genetic basis for cardiovascular disease. The specific objectives of the analysis presented hereinbelow are to retrospectively study the INR fluctuations outside of a target therapeutic INR range, and to test for the contribution of selected candidate genes to fluctuation risk in a subset of 324 patients. INR fluctuations represent an important facet of warfarin adverse event management which can appear even after having reached a stable maintenance dose of warfarin. The identification of patients at an increased risk for fluctuations could support the establishment of targeted monitoring practices and allow for the selection of patients who would benefit from the new FXa inhibitors. The rapid identification of those high risk patients could offer a considerable health benefit by reducing the risk of adverse outcomes in those patients.

Other objects, advantages and features of the present invention will become more apparent upon reading of the following non-restrictive description of preferred embodiments thereof, given by way of example only with reference to the accompanying drawings.

Additional objects, advantages and novel features of the technology will be set forth in part in the description which follows, and in part will become more apparent to those skilled in the art upon examination of the following, or may be learned from practice of the technology.

BRIEF DESCRIPTION OF THE DRAWINGS

Non-limiting and non-exhaustive embodiments of the present invention, including the preferred embodiment, are described with reference to the following figures, wherein like reference numerals refer to like parts throughout the various views unless otherwise specified. Illustrative embodiments of the invention are illustrated in the drawings, in which:

FIG. 2: in a table form, illustrates genetic association test results of a pilot study of INR fluctuations in 324 post INR-stabilization patients from the MHI warfarin clinic.

DETAILED DESCRIPTION

Figure 1:
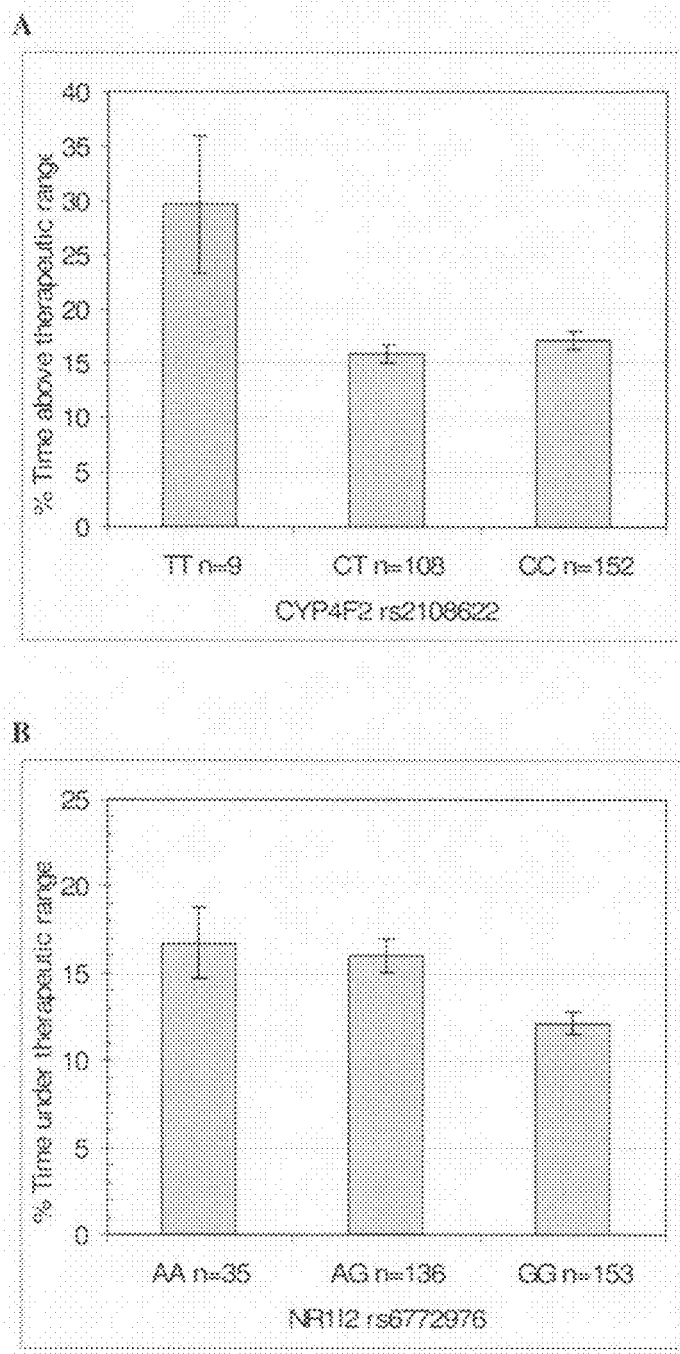
FIG. 1: illustrates specific results of a pilot study of INR fluctuations in 324 post INR-stabilization patients from the MHI warfarin clinic: panel a: Mean and standard error for the % time above the target therapeutic INR range by CYP4F2 rs2108622 genotypes; panel b: mean and standard error for the % time under the target therapeutic INR range by NR1I2 rs6772976 genotypes.

Embodiments are described more fully below in sufficient detail to enable those skilled in the art to practice the system and method. However, embodiments may be implemented in many different forms and should not be construed as being limited to the embodiments set forth herein. The following detailed description is, therefore, not to be taken in a limiting sense.

The Montreal Heart Institute (MHI) has a large anticoagulation clinic, which follows in excess of 4200 patients on long-term warfarin therapy. Patients attending this clinic were recruited to participate in a study aimed at uncovering the genetic basis for cardiovascular disease. The specific objectives were to retrospectively study the INR fluctuations outside of a target therapeutic INR range, and to test for the contribution of selected candidate genes to fluctuation risk in a subset of 324 patients. INR fluctuations represent an important facet of warfarin adverse event management which can appear even after having reached a stable maintenance dose of warfarin. The identification of patients at an increased risk for fluctuations could support the establishment of targeted monitoring practices and allow for the selection of patients who would benefit from the new FXa inhibitors. The rapid identification of those high risk patients could offer a considerable health benefit by reducing the risk of adverse outcomes in those patients.

It should be noted that in this study, INR fluctuations in time for a stable warfarin dose were examined. In other words, some patients show a time-varying response to warfarin that results in undesirable variations in time of their INR even when an optimal warfarin dose has been determined. This is to be contrasted to the majority of prior art genomic studies regarding warfarin dosage that seek to identify genotypes that could predict the optimal warfarin dose.

In a study conducted at the Montreal Heart Institute, a pilot observational retrospective study was performed to evaluate whether a patient's genetic information can predict risk of INR fluctuation in the post INR-stabilization. Data from a retrospective study on 1,615 patients recruited at the MHI warfarin clinic was used. Computerized laboratory test results of patients dating back to December 2001 was obtained, along with information on primary indication for warfarin therapy, warfarin start date and target therapeutic INR range from the warfarin clinic medical chart. Based on the records of 1,615 patients, the average follow-up time was 60.8 months. The study was focused on the post INR-stabilization period by excluding the first six months of therapy, and further excluded hospitalization periods. The primary indications for warfarin therapy were atrial fibrillation (59.7%) (chronic, paroxystic or post-operative included) and mechanical valve replacement (29%). The INR target therapeutic INR range was set to 2-3 in 68.4% of patients and to 2.5-3.5 in the remaining patients. Patients were found above their target therapeutic INR range 17.2% of the time during the post-stabilization follow up period, and 14.1% of the time below the range. INR fluctuations were measured according to the Rosendaal method based on linear interpolation.

For the pilot genetic study, 324 patients with atrial fibrillation were selected, for whom therapy was started prior to Aug. 1, 2005, with a follow up of 36 months or more and with at most 70 years of age. Following a literature review on warfarin genetics and pharmacokinetics, 30 single-nucleotide polymorphisms (SNPs) were selected in 19 candidate genes for genotyping. Genotyping was conducted using the Sequenom technology.

Genetic association results are reported in the table of FIG. 2. After adjustments for the multiple genetic tests, a significant association was found between the CYP4F2 rs2108622 variant and percent time above the patient-specific target therapeutic INR range (p=0.0005). Patients with the TT genotype were on average 29.6% of the time above the range, compared to CT and CC genotype carriers who were 15.9% and 17.1% of the time above the range respectively (FIG. 1, panel a). A significant association was found between rs6772976 in the NR1I2 gene coding for the pregnane X receptor (PXR), a known inducer of cytochrome enzymes, and % time spent below the target therapeutic INR range. Patients with the AA and AG genotypes spent on average 16.8% and 16.0% time below the range respectively, compared to 12.2% of the time for patients with the GG genotype (p=0.0005) (FIG. 1, panel b).

An association was found between genetic polymorphisms in CYP4F2 and NR1I2 and INR fluctuation in the post-stabilization period of warfarin treatment. This is the first known report of such an association. This finding offers new potential for the development of pharmacogenetic tests that could assist clinicians in the identification of patients at a higher risk of serious events when treated with warfarin, and who could benefit from the use of an alternative treatment. Optimizing the management of warfarin therapy may not only improve the prevention of bleeding and thromboembolic events, but may also provide a considerable health benefit and decrease in associated health-care costs.

In another embodiment, there may be provided a kit for identifying a subject having genetic predictors of predisposition to abnormal international normalized ratio (INR) fluctuation during warfarin therapy. The kit may include a test to check the subject for a presence of a predetermined genetic variation. The predetermined genetic variation is correlated with abnormal INR fluctuation during warfarin therapy. The kit may also include an indicator to identify the presence of the predetermined genetic variation so as to identify the subject as having a predisposition to abnormal INR fluctuation during warfarin therapy. In an embodiment, the kit may be configured for a human subject.

In an embodiment, the predetermined genetic variation is a predetermined single nucleotide polymorphism (SNP). In one embodiment, the predetermined SNP may be correlated with the abnormal INR fluctuation being generally below a patient-specific target therapeutic INR range The presence of that predetermined SNP identifies the subject as having a predisposition to the abnormal INR fluctuation being generally below the patient-specific target therapeutic INR range. In another embodiment, the predetermined SNP may be correlated with the abnormal INR fluctuation being generally above a patient-specific target therapeutic INR range. The presence of this predetermined SNP identifies the subject as having a predisposition to the abnormal INR fluctuation being generally above the patient-specific target therapeutic INR range.

In an embodiment, the patient-specific target therapeutic INR range is set to 2-3. In another embodiment, the patient-specific target therapeutic INR range is set to 2-3. In an embodiment, the test to check the subject for the presence of the predetermined genetic variation is conducted during a post-stabilization period of the warfarin therapy.

In one embodiment, the test may be configured to check the subject for the predetermined genetic variation in the CYP4F2 gene. The test may also be configured to check the subject for the predetermined genetic variation in a predetermined single nucleotide polymorphism (SNP) in the CYP4F2 gene. In one embodiment, the predetermined SNP in the CYP4F2 gene is rs2108622. The predetermined SNP may be correlated with the abnormal INR fluctuation being generally above a patient-specific target therapeutic INR range. The presence of the predetermined SNP identifies the subject as having a predisposition to the abnormal INR fluctuation being generally above the patient-specific target therapeutic INR range.

In another embodiment, the test may be configured to check the subject for the predetermined genetic variation in the NR1I2 gene. The test may be configured to check the subject for the predetermined genetic variation in a predetermined single nucleotide polymorphism (SNP) in the NR1I2 gene. In one embodiment, the predetermined SNP in the NR1I2 gene is rs6772976. The predetermined SNP may be correlated with the abnormal INR fluctuation being generally below a patient-specific target therapeutic INR range. The presence of the predetermined SNP identifies the subject as having a predisposition to the abnormal INR fluctuation being generally below the patient-specific target therapeutic INR range.

The test to check the subject for the presence of the predetermined genetic variation may include performing a hybridization reaction followed by fluorescence in situ hybridization. The test to check the subject for the presence of the predetermined genetic variation may include performing one or more of a DNA sequencing procedure, a PFGE analysis procedure, a Southern blot analysis procedure, a single stranded conformation analysis procedure, and a RNase protection assay procedure, among other suitable procedures.

Although the above embodiments have been described in language that is specific to certain structures, elements, compositions, and methodological steps, it is to be understood that the technology defined in the appended claims is not necessarily limited to the specific structures, elements, compositions and/or steps described. Rather, the specific aspects and steps are described as forms of implementing the claimed technology. Since many embodiments of the technology can be practiced without departing from the spirit and scope of the invention, the invention resides in the claims hereinafter appended.

What is claimed is:

1. A method of determining risk of INR fluctuations following warfarin dose stabilization and providing anti-coagulation therapy to a subject in need thereof, the method comprising:
    analyzing a polymorphism at the polymorphic site rs6772976 in a nucleic acid sample obtained from the subject using a DNA hybridization or DNA sequencing method;
    determining a genotype at the polymorphic site rs6772976; and
    treating the subject with warfarin if the genotype is GG or treating the subject with an alternative therapy to warfarin if the genotype is AA or AG.

2. The method of claim 1, wherein the step of determining the genotype at rs6772976 includes performing a hybridization reaction followed by fluorescence in situ hybridization.

3. The method of claim 1, wherein the step of determining the genotype at rs6772976 includes performing at least one of a DNA sequencing procedure, a PFGE analysis procedure, a Southern blot analysis procedure, a single stranded conformation analysis procedure, and a RNase protection assay procedure.

4. The method of claim 1, wherein said genotype is determined before a dose-stabilization period of warfarin therapy.

5. The method of claim 1, wherein said genotype is determined after a dose-stabilization period of warfarin therapy.

6. The method of claim 1, wherein the step of determining the genotype at rs6772976 includes performing a DNA sequencing procedure.

7. The method of claim 1, wherein the subject carries the GG genotype further comprising treating the subject with warfarin.

8. The method of claim 1, wherein the subject carries an AG genotype further comprising treating the subject with said alternative therapy to warfarin.

9. The method of claim 8, wherein said alternative therapy is an Fxa inhibitor.

10. The method of claim 1, wherein the subject carries an AA genotype and further comprising treating the subject with said alternative therapy to warfarin.

11. The method of claim 10, wherein said alternative therapy is an Fxa inhibitor.

* * * * *